(12) United States Patent
Diedering et al.

(10) Patent No.: US 11,000,000 B2
(45) Date of Patent: May 11, 2021

(54) REPOSITIONING WIRES AND METHODS FOR REPOSITIONING PROSTHETIC HEART VALVE DEVICES WITHIN A HEART CHAMBER AND RELATED SYSTEMS, DEVICES AND METHODS

(71) Applicant: 4C MEDICAL TECHNOLOGIES, INC., Maple Grove, MN (US)

(72) Inventors: Jason S. Diedering, Minneapolis, MN (US); Saravana B. Kumar, Minnetonka, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 0 days.

(21) Appl. No.: 16/568,903

(22) Filed: Sep. 12, 2019

(65) Prior Publication Data

US 2020/0085571 A1 Mar. 19, 2020

Related U.S. Application Data

(60) Provisional application No. 62/731,230, filed on Sep. 14, 2018.

(51) Int. Cl.
*A61F 2/24* (2006.01)
*A61F 2/90* (2013.01)
*A61F 2/966* (2013.01)

(52) U.S. Cl.
CPC .............. *A61F 2/243* (2013.01); *A61F 2/90* (2013.01); *A61F 2/966* (2013.01)

(58) Field of Classification Search
CPC ................ A61F 2/95; A61F 2002/9505; A61F 2002/9511; A61F 2002/9665; A61B 2017/00623
See application file for complete search history.

(56) References Cited

U.S. PATENT DOCUMENTS

| 4,878,906 A | * | 11/1989 | Lindemann ............... A61F 2/91 623/3.18 |
| 5,843,090 A | | 12/1998 | Schuetz |
| 2006/0184226 A1 | | 8/2006 | Austin |

(Continued)

OTHER PUBLICATIONS

International Search Report and Written Opinion, dated Nov. 15, 2019, for PCT Application No. PCT/US2019/050978, filed Sep. 13, 2019.

*Primary Examiner* — Todd J Scherbel
(74) *Attorney, Agent, or Firm* — Barnes & Thornburg LLP; Jeffrey R. Stone

(57) ABSTRACT

The invention provides methods, devices and systems for delivering, positioning and/or repositioning an expandable prosthetic heart valve in a patient's heart chamber. At least one non-looped wire and looped wire pair is operatively connected with an expanded prosthetic heart valve that is collapsed within a delivery catheter lumen having its distal end positioned in the subject heart chamber. The collapsed prosthetic heart valve is translated through the delivery catheter lumen to and out of its distal end where the prosthetic heart valve expands to a working configuration. The wire(s) of the non-looped and looped wire pair may be manipulated by pulling proximately or pushing distally to position or reposition the expanded prosthetic stent into position, then released from connection with the positioned stent and withdrawn from the patient.

11 Claims, 2 Drawing Sheets

(56) References Cited

U.S. PATENT DOCUMENTS

| | | | |
|---|---|---|---|
| 2007/0233223 A1* | 10/2007 | Styrc | A61F 2/2439 |
| | | | 623/1.11 |
| 2009/0099640 A1* | 4/2009 | Weng | A61F 2/95 |
| | | | 623/1.11 |
| 2014/0379020 A1 | 12/2014 | Campbell et al. | |
| 2015/0127032 A1 | 5/2015 | Lentz et al. | |
| 2015/0148731 A1 | 5/2015 | McNamara et al. | |
| 2017/0165066 A1* | 6/2017 | Rothstein | A61F 2/2418 |

\* cited by examiner

REPOSITIONING WIRES AND METHODS FOR REPOSITIONING PROSTHETIC HEART VALVE DEVICES WITHIN A HEART CHAMBER AND RELATED SYSTEMS, DEVICES AND METHODS

CROSS-REFERENCE TO RELATED APPLICATIONS

This application claims the benefit of U.S. Provisional Application Ser. No. 62/731,230, filed Sep. 14, 2018 and entitled REPOSITIONING WIRES AND METHODS FOR REPOSITIONING PROSTHETIC HEART VALVE DEVICES WITHIN A HEART CHAMBER, the entire contents of which are incorporated herein by reference.

STATEMENT REGARDING FEDERALLY SPONSORED RESEARCH OR DEVELOPMENT

Not Applicable

INCORPORATION BY REFERENCE

All references, including but not limited to publications, patent applications and patents mentioned in this specification are hereby incorporated by reference to the same extent and with the same effect as if each reference was specifically and individually indicated to be incorporated by reference.

FIELD OF THE INVENTION

The inventions described herein relate to delivery systems, devices and methods for delivering and/or positioning a cardiac valve.

BACKGROUND OF THE INVENTION

The human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of.

Native heart valves may be, or become, dysfunctional for a variety of reasons and/or conditions including but not limited to disease, trauma, congenital malformations, and aging. These types of conditions may cause the valve structure to either fail to properly open (stenotic failure) and/or fail to close properly (regurgitant).

Mitral valve regurgitation is a specific problem resulting from a dysfunctional mitral valve. Mitral regurgitation results from the mitral valve allowing at least some retrograde blood flow back into the left atrium from the right atrium. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and transseptal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

However, known delivery systems, devices and methods still suffer from significant flaws in delivery methodology including, inter alia, positioning, repositioning and/or recapture capability and efficiency.

Various embodiments of the several inventions disclosed herein address these, inter alia, issues.

BRIEF SUMMARY OF THE INVENTION

The invention provides methods, devices and systems for delivering, positioning and/or repositioning an expandable prosthetic heart valve in a patient's heart chamber. At least one non-looped wire and looped wire pair is operatively connected with an expanded prosthetic heart valve frame that is collapsed within a delivery catheter lumen having its distal end positioned in the subject heart chamber. The collapsed prosthetic heart valve frame is translated through the delivery catheter lumen to and out of its distal end where the prosthetic heart valve expands to a working configuration. The wire(s) of the non-looped and looped wire pair may be manipulated by pulling proximately or pushing distally to position or reposition the expanded prosthetic stent into position, then released from connection with the positioned stent and withdrawn from the patient.

DETAILED DESCRIPTION OF THE INVENTION

Various embodiments of the present invention are disclosed in the Figures for providing percutaneous access to the valve of interest via one of at least the following known access routes: transapical; transfemoral; transatrial; and transseptal delivery techniques. Each of these access routes may be used for the embodiments disclosed herein.

Figure 1:
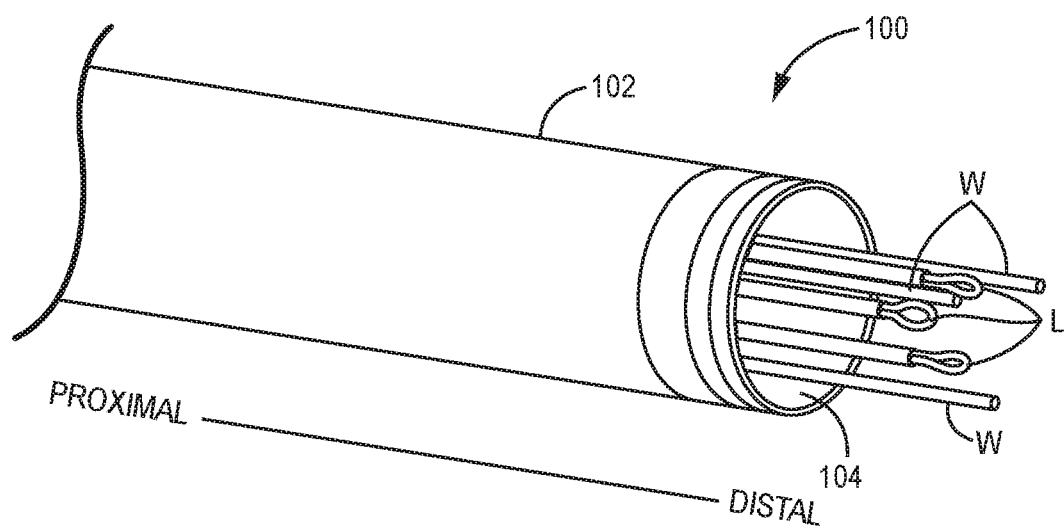
FIG. 1 illustrates a perspective view of a distal end of one embodiment of the present invention.

FIG. 1 illustrates the distal end of an exemplary embodiment of system 100 comprising a set of positioning/release wire and loop pairs that are translatable and rotatable within the lumen of a delivery catheter or sheath, and extending distally outwardly away from the distal end of the delivery catheter or sheath 102 and the lumen 104 defined therethrough. Each pair consists of a looped wire L and a non-looped wire W. As shown, three pairs of non-looped wires W and looped L wires are provided, though the skilled artisan will recognize that as few as one pair and more than three pairs of wires may be employed. Each non-looped wire W may be threaded around or otherwise operatively connected with one or more struts of an exemplary stent and further threaded through a loop formed at the distal end of the looped wire L to form the non-looped and looped wire pair, preferably at a junction between two struts forming a portion of a stent cell, and as will be discussed further below.

It is advantageous from positioning and repositioning perspectives, once the stent has been delivered and expanded within a heart chamber, to provide the non-looped wire W and looped wire L pair connections at spaced-apart locations on the stent frame to optimize the operator's ability to change the position of the expanding or expanded frame. Thus, a first wire pair may be provided on one side of the stent frame a second wire pair may be provided on the other side of the stent frame. In this system, it is now possible for the operator to manipulate the position of the expanded stent frame by pulling proximally and/or pushing distally on one or more of the wires and/or loops and/or wire and loop pairs. A third wire pair may be provided at another location spaced apart from the first and second wire pairs to further enhance repositioning and manipulation capabilities, e.g., near the upper portion of the expanded stent. These connection locations are merely exemplary, the skilled artisan will recognize that a plurality of such locations are possible, each of which are within the scope of the present invention.

Figure 2:
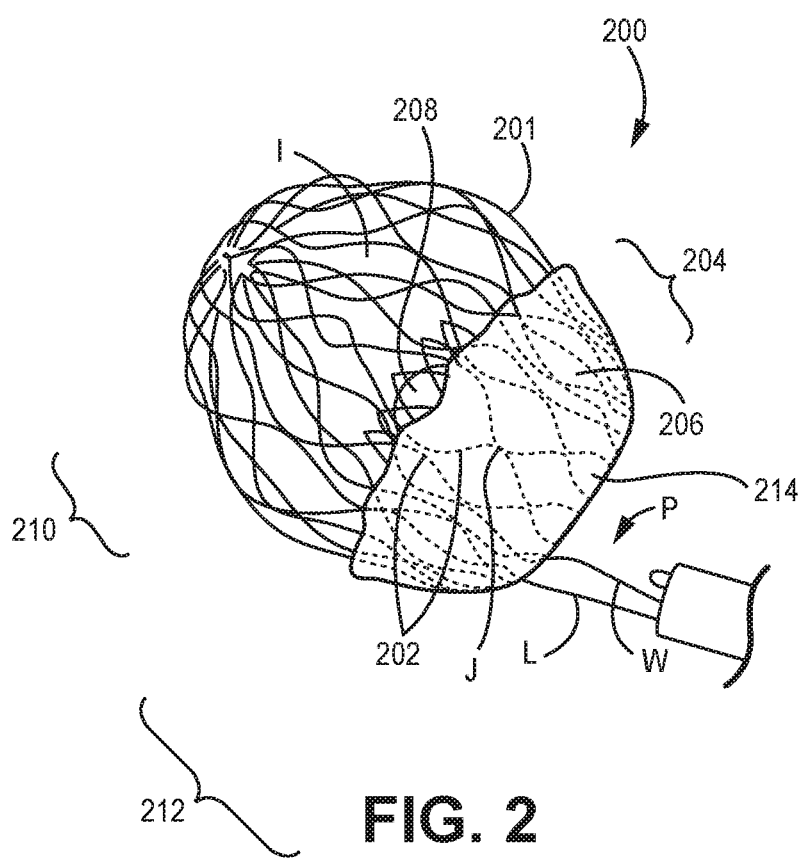
FIG. 2 illustrates a perspective view of one embodiment of the present invention.

FIG. 2 illustrates one such non-looped wire W and looped wire L pair P comprising an interconnected non-looped wire W and looped wire L and connection with an expandable and collapsible prosthetic mitral valve 200 defined by a stent frame 201 formed by interconnecting struts 202 that form or define cells C, wherein the cells C are formed by junction points J where two struts 202 are operatively engaged or interconnected as shown. In the exemplary prosthetic heart valve of FIG. 2, a portion of the lower outer surface 204 is covered by a fabric skirt 206 and the valve support 208 with associated prosthetic leaflets attached thereto (not shown) is disposed within the interior I defined by the stent frame 201. The exemplary prosthetic mitral valve thus provides a one-way flow from the upper region 210 to the lower region 212, with the leaflets performing the valving function as the skilled artisan will recognize. Thus, an expanded and exemplary prosthetic mitral valve will occupy the left atrium, with a lower surface 214 residing on an upper annular surface within the left atrium, wherein the valve support provides a flow path through the leaflets and into and through the annulus leading to the left ventricle.

In this exemplary and illustrated case, the wire and loop connection forming the connected wire pair P is made at a lower or distal end, within the lower region 212, of the prosthetic heart valve, operatively engaging and connecting to a junction J between two struts 202 as shown. Because the fabric skirt 206 covers the subject struts 202 and junction J formed therebetween, the non-looped wire W and/or looped wire L may penetrate the fabric to reach and connect with the subject strut. Further, as shown, the wire and loop connection described above is made preferably at a junction J of two struts 202, wrapping around the junction J to prevent both unwanted sliding of the connection along the struts 202 which may result in unwanted tearing of the fabric skirt 206. As discussed above, two or more, or a plurality, of non-looped and looped wire pairs P may also be connected in the same or similar manner and in spaced-apart relation to a first non-looped and looped wire pair P. Since the non-looped and looped wire pair(s) P are operatively connected to strut junction(s) D at a distal or lower end of the prosthetic mitral valve device as shown, in a transseptal delivery to the left atrium, the upper region 210 of the stent 201 will exit the lumen 104 of the delivery catheter 102 into the left atrium first, before the distal or lower end or region 212 of the stent. The connected wire pairs P may be used to turn and position the expanded stent 201 so that the lower surface 214 is at least partially engaged with an upper annular surface within the left atrium.

It is to be understood that the non-looped and looped pair(s) P are connected before collapsing the prosthetic heart valve stent frame 201 into the proximal end and lumen 104 of the delivery catheter 102 for translational delivery therealong to the subject heart chamber where expansion of the prosthetic heart valve frame occurs when it is released from the distal end of the lumen 104 of the delivery catheter 102. Thus the non-looped and looped wire pair(s) P may extend through the lumen 104 of the delivery catheter 102 and comprise a length that allows a distal end to reach the subject heart chamber while allowing an operator to manipulate the proximal ends of the non-looped wires W and looped wires L connected in wire pair(s) P. Further, in some embodiments, more than one non-looped positioning wire W may be combined with a looped wire W. In other embodiments, more than one looped wire L may be combined with one non-looped wire W.

In this system, therefore, the skilled artisan will now appreciate that the expanded stent 201 may be manipulated in one or more planes using the non-looped W and looped L wires as push and/or pull wires, either as pairs P of wires moving relative to each other and/or the individual non-looped W and looped L wires moving relative to each other to manipulate the stent's position from the proximal end.

Figure 3:
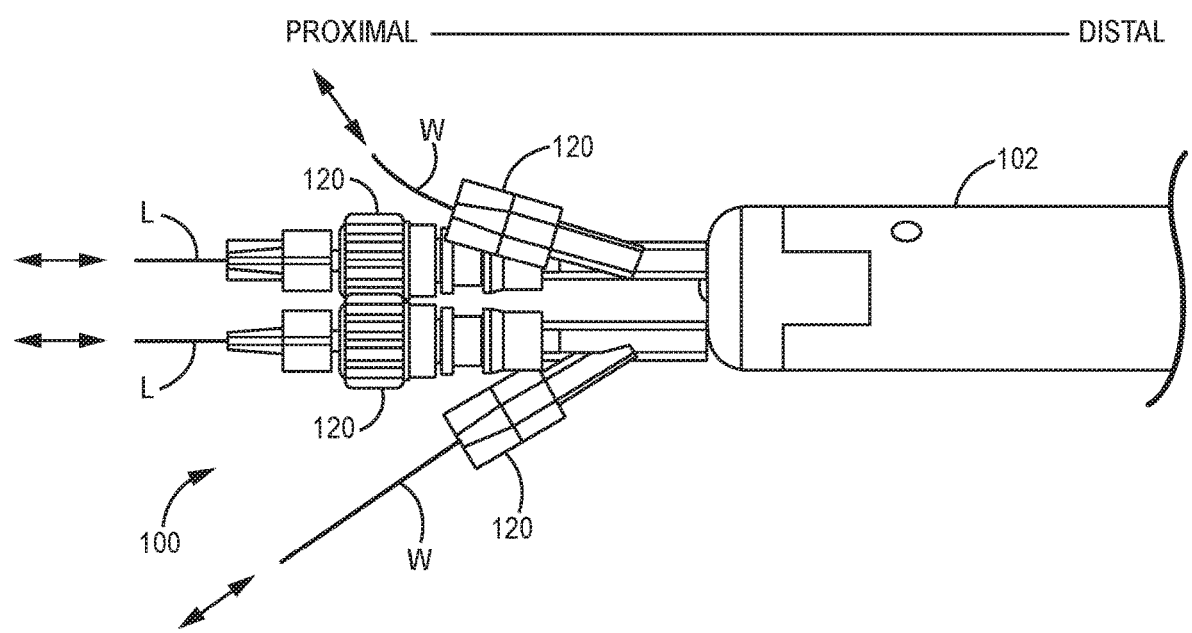
FIG. 3 illustrates a side, cutaway view of a proximal end of one embodiment of the present invention.

FIG. 3 illustrates an exemplary proximal end of a delivery device 100 illustrating two repositioning/release wire and loop pairs P, wherein each looped wire L of a pair P may be connected with a luer lock, or equivalent, device 120 that may be used to lock or unlock/release one or both of the non-looped W and looped L wires of the pair P. Locking one or both wires L, W of the pair P fixes the relative location and movement of the locked wire(s) until unlocked or released. The operator may manipulate the position of the stent 201 if all locks 102 are engaged by pushing and/or pulling on one or more of the wire pairs P. Unlocking one or both wires L, W of a pair P enables an operator from the proximal end to push and/or pull wire(s) L, W, and therefore position and/or reposition the expanding and/or expanded stent to which the wire and loop pair(s) P is/are connected. As discussed above, there may be one, two, three or more such wire and loop pairs P within the device. Unlocking both wires L, W of the pair P allows translation and rotation of each wire L, W and relative to each other.

As further discussed herein, the exemplary prosthetic heart valve 200 comprising the expandable and collapsible stent frame 201 of FIG. 2 may comprise one or more wire and loop pairs P connected with a lower or distal region 212 of the expanded heart valve. Next, the expanded prosthetic heart valve is collapsed within the delivery catheter lumen 104 at its proximal end and translated in the collapsed configuration to the patient's left atrium where it is released and expanded to a working configuration as shown in FIG. 2. Either the upper end or upper region 210, or the lower end or distal region 212 may be first collapsed and introduced into the lumen 104 of delivery catheter 102. When the stent frame 201 emerges, or begins to emerge, from the distal end of lumen 104 of delivery catheter 102, the wire pair(s) P may be used to manipulate or change the position of expanding or expanded stent frame 201 to orient the lower surface 214 of the stent and the associated valve support 208 and prosthetic leaflets with the native annulus and mitral valve. This positioning may be done by manipulating the wire and loop pairs(s) P, and/or the individual non-looped W and looped L wire(s) in order to align the stent 201 and fluid flow path therethrough with the native annulus to enable fluid communication therewith and therethrough. Moreover, if the initial positioning of the prosthetic valve device 200 is not optimal, the wire and loop pair(s) P, and/or the individual non-looped W and looped L wire(s), may be used to manipulate and reposition until optimal placement is achieved. At that point, the wire and loop pair(s) P may be disconnected from the stent frame 201 and withdrawn proximally through the delivery catheter lumen 104.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A method for delivering, positioning and/or repositioning a collapsible and expandable stent having a stent frame within a patient's heart chamber, comprising:
   providing at least three non-looped wire and looped wire pairs, wherein a distal end of each of the at least three wire pairs is operatively and releasably connected with a corresponding junction between two struts of the stent such that, for each of the at least three non-looped wire and looped wire pairs, the non-looped wire wraps around the junction and extends through a loop formed on the distal end of the looped wire, and wherein proximal ends of each wire in the at least three wire pairs extend outside the patient;
   providing a delivery catheter comprising a lumen with a proximal end and a distal end;
   positioning the distal end of the delivery catheter within the heart chamber;
   advancing the stent in an expanded configuration into the proximal end of the lumen of the delivery catheter and collapsing the stent to a collapsed configuration;
   translating the collapsed stent in the collapsed configuration distally through the lumen of the delivery catheter;
   delivering the collapsed stent out of the distal end of the lumen of the delivery catheter and expanding the stent to an expanded working configuration;
   manipulating the proximal ends of each wire in the at least three non-looped wire and looped wire pairs to position the expanded stent within the patient's heart chamber;
   releasing the non-looped wire from the looped wire to disconnect each of the at least three non-looped wire and looped wire pairs from the expanded and positioned stent; and
   withdrawing each non-looped wire and looped wire proximally through the delivery catheter lumen.

2. The method of claim 1, wherein the patient's heart chamber comprises the left atrium and the delivery catheter is positioned to provide a transseptal delivery of the expanded stent into the left atrium.

3. The method of claim 2, wherein the stent comprises a lower end and an upper end, wherein the lower end is positioned adjacent to the patient's native mitral valve.

4. The method of claim 1, wherein the delivery catheter is positioned to provide access to the patient's heart chamber by one of the group of delivery techniques consisting of: transapical; transfemoral; transatrial; and transseptal.

5. The method of claim 4, wherein the junction between the two struts is located at a lower end of the stent.

6. The method of claim 4, wherein the stent comprises a lower outer surface at least partially covered by a fabric skirt, wherein the at least three non-looped wire and looped wire pairs extend through the fabric skirt, and wherein the junction between the two struts is located at the lower end of the stent.

7. The method of claim 1, wherein each wire pair of the at least three wire pairs engaging a junction between two struts at a location that is spaced apart from the other wire pairs.

8. The method of claim 7, further comprising providing a releasable lock operatively engaging each looped wire of the at least three non-looped and looped wire pairs.

9. The method of claim 1, further comprising providing a releasable lock operatively engaging the proximal end of the non-looped wire in each of the at least three non-looped and looped wire pairs.

10. The method of claim 9, wherein locking the releasable lock corresponding to one of the at least three non-looped and looped wire pairs prevents the non-looped and looped wires of that wire pair from moving relative to each other.

11. The method of claim 9, wherein unlocking the releasable lock from the non-looped wire of one of the at least three non-looped and looped wire pairs allows relative movement between the non-looped wire and the looped wire of that non-looped and looped wire pair.

\* \* \* \* \*